United States Patent [19]

Edelman

[11] 4,276,026
[45] Jun. 30, 1981

[54] ANGULATION HEAD FOR DENTAL IMPLANT AND BENDING TOOL FOR SAME

[76] Inventor: Alfred E. Edelman, Haddon View South 802, 1 MacArthur Blvd., Westmont, N.J. 08108

[21] Appl. No.: 149,457

[22] Filed: May 13, 1980

Related U.S. Application Data

[60] Division of Ser. No. 937,585, Aug. 28, 1978, Pat. No. 4,217,100, which is a continuation-in-part of Ser. No. 819,119, Jul. 26, 1977, abandoned, which is a continuation of Ser. No. 559,226, Mar. 17, 1975, abandoned.

[51] Int. Cl.³ ............................................. A61C 8/00
[52] U.S. Cl. ...................................... 433/176; 433/141
[58] Field of Search ........................ 433/173, 176, 141

[56] References Cited

U.S. PATENT DOCUMENTS

| | | | |
|---|---|---|---|
| 3,690,005 | 9/1972 | Edelman | 433/176 |
| 4,109,383 | 8/1978 | Reed | 433/176 |

Primary Examiner—Robert Peshock
Attorney, Agent, or Firm—Munson H. Lane, Jr.

[57] ABSTRACT

An angulation head for removable attachment to a dental implant of a type having a hollow interiorly threaded neck integrally attached to an implant portion comprises a stem at least a portion of which is exteriorly threaded and adapted to be screwed into the hollow neck, an integral cap, or flange to seat on top of the neck and a bendable upstanding head portion which is adaptable to be bent angularly with respect to the cap and stem by use of a manual bending tool. The bending tool comprises a hand held elongated holder for the angulation head and an elongated bending shaft for bending the head portion. The hand held holder includes an elongated handle having at one end a flat surface normal to the axis of the handle and an axial socket extending inwardly from said flat end for receiving the stem of the angulation head with the cap seated on the flat end, the socket having interior threads for engaging the threaded portion of the stem. The elongated bending shaft has an axially extending socket at one end which is closed at its inner end and which is open at its outer end to snugly receive the bendable head portion of the angulation head.

7 Claims, 9 Drawing Figures

U.S. Patent    Jun. 30, 1981    4,276,026
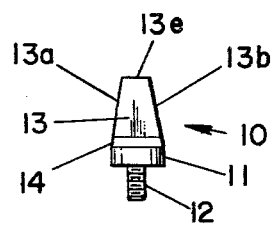
FIG. 1
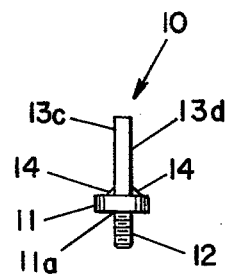
FIG. 2
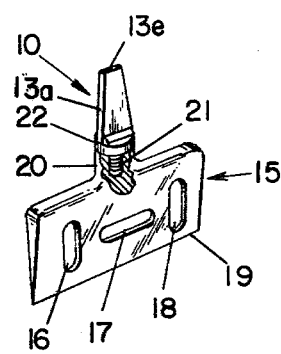
FIG. 3
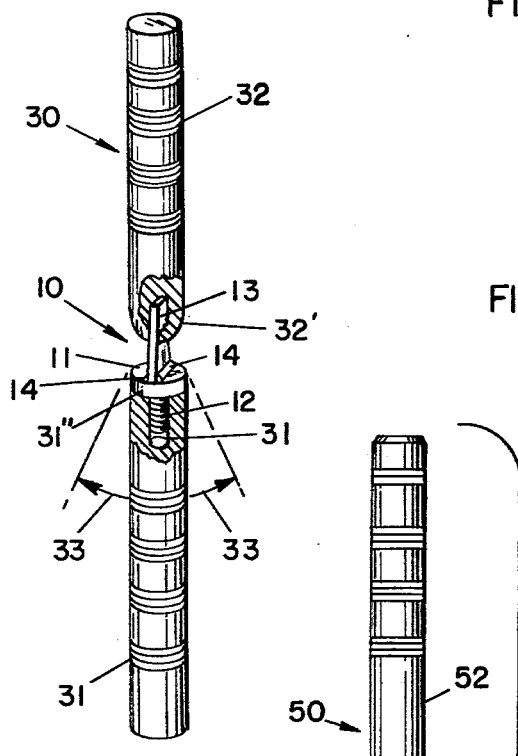
FIG. 4
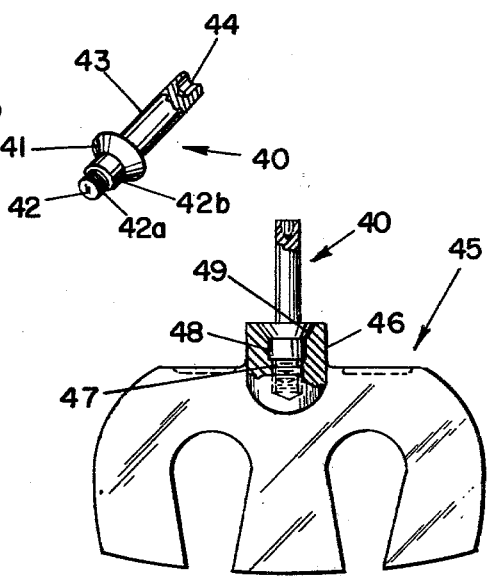
FIG. 5
FIG. 6
FIG. 7
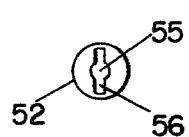
FIG. 9
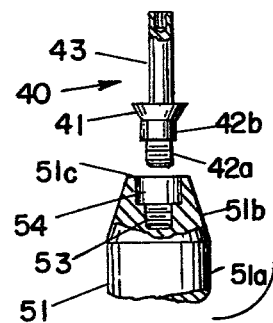
FIG. 8

ANGULATION HEAD FOR DENTAL IMPLANT AND BENDING TOOL FOR SAME

CROSS REFERENCE TO RELATED APPLICATIONS

This application is a division of Ser. No. 937,585, filed Aug. 28, 1978 and now U.S. Pat. No. 4,217,100 issued Aug. 12, 1980 which is a continuation-in-part of my application Ser. No. 819,119, filed July 26, 1977 and now abandoned, for Submerged Functional Implant and Method, which is a continuation of my application Ser. No. 559,226 filed Mar. 17, 1975, now abandoned.

BACKGROUND OF THE INVENTION

This invention relates to an improved angulation head for removable attachment to a dental implant of a type having a hollow interiorly threaded neck to which the angulation head is adapted to be removably attached, and an implant portion adapted to be implanted in the jaw of a human or other animal, and to a bending tool for bending the angulation head so that a portion of the angulation head will extend in a desired angular direction with respect to the implant portion to which it is to be attached.

With the development in dental implant technology of submerged functional implants as disclosed in my prior patent applications, Ser. No. 819,119, and Ser. No. 559,226, referred to above, the use of removable heads for dental implants has become important. The implant portion of the submerged functional implant is implanted in the jaw and the tissue covering the jaw is sutured over the implant for sufficient time to permit the bone to heal and intermesh with the implant portion. After the implant portion has been implanted for sufficient time, the skin covering the neck of the implant portion is slit and pulled away sufficiently so that a separate head can be attached to the implant portion.

Sometimes it may be necessary or desirable to change the angularity of the head relative to the implant portion. Once the implant portion has become set in the jaw, it is not desirable to move it, thus it is an object of the present invention to provide an improved bendable angulation head for a dental implant.

It is a further object of this invention to provide an angulation head which comprises an intermediate cap or flange portion, an integral stem depending from the cap, and an upstanding bendable head portion integrally attached to the cap opposite the stem. In one embodiment of the invention, the stem is threaded throughout its length. In another embodiment of the invention, the stem is threaded only at its tip end and is unthreaded for a portion of its length intermediate the cap and the threaded tip portion.

The cap of the angulation head may be cylindrical with a flat underside or it may have an inverted conical undersurface which tapers to the unthreaded portion of the stem. The head portion of the angulation head may be cylindrical in cross section and adapted to be bent in any direction of a full circle, or it may be rectangular in cross section having a pair of broad flat parallel opposite sides and a pair of narrow opposite sides which taper toward a flat top, the latter head portion being bendable only laterally relative to the broad sides thereof.

It is another object of the invention to provide a bending hand tool for use in bending the improved angulation head of this invention. The bending tool comprising an elongated holder for supporting the angulation head by its stem and a hand manipulatable elongated bending shaft for engaging the bendable head portion of the angulation head.

It is a further object of the invention to provide a bending hand tool in which the elongated holder comprises an elongated handle having a flat end normal to the axis of the handle on which the cap portion of the angulation head rests, and an axial socket for receiving the stem of the angulation head, the socket having interior threads for engaging the exterior threads of the stem of the angulation head. In a preferred embodiment of the invention the socket of the holder is threaded for only a portion of its length adjacent the bottom or inner end thereof and is provided with a coaxial counterbore adjacent its outer end which is of greater diameter than the diameter of the stem of the angulation head.

It is still a further object of this invention to provide an elongated bending shaft which has an axially extending socket which is closed at its inner end and which is open at its outer end to snugly receive the bendable head portion of the angulation head. In the preferred embodiment of the invention, the socket of the bending shaft is formed with a central cylindrical socket to receive a cylindrical angulation head and with a rectangular slot to receive an angulation head of rectangular cross section.

BRIEF DESCRIPTION OF THE DRAWINGS

With the foregoing more important objects and features in view and such other objects and features which may become apparent as this specification proceeds, the invention will be understood from the following description taken in conjunction with the accompanying drawing, in which like characters of reference are used to designate like parts, and in which:

FIG. 1 is a front elevational view of an angulation head for the functional submerged implant shown in FIG. 3.

FIG. 2 is a side elevational view of the angulation head shown in FIG. 1.

FIG. 3 is a perspective view of a functional submerged implant for use in combination with the head shown in FIGS. 1 and 2.

FIG. 4 is a partial sectional view of the bending tool of this invention for the angulation head shown in FIGS. 1 and 2.

FIG. 5 is a perspective view of another embodiment of an angulation head in accordance with this invention.

FIG. 6 is a perspective view of a functional submerged implant for use in combination with the angulation head shown in FIG. 5.

FIG. 7 is an exploded, partly sectional view of another embodiment of the bending tool of this invention with the angulation head shown in FIG. 5.

FIG. 8 is a partial sectional view of the angulation head holder portion of the bending tool shown in FIG. 7 with the angulation head of FIG. 5 fully seated in the holder socket.

FIG. 9 is an end view of the bending shaft portion of the bending tool shown in FIG. 7.

DETAILED DESCRIPTION OF THE PREFERRED EMBODIMENTS

Referring now to FIGS. 1 and 2, one embodiment of the angulation head of this invention is generally indicated by the reference numeral 10. The angulation head 10 comprises a cylindrical cap portion 11, an exteriorly threaded stem 12, and a thin flat upstanding head portion 13. The head portion 13 has broad parallel opposite front and back faces 13c and 13d and sloping side surfaces 13a and 13b which slope inwardly from the juncture of the head with the cap portion 11 toward a flat top 13e which is parallel with the cap portion 12. The top of the cap portion 11 is beveled inwardly at 14 toward the head portion 13. The head portion 13 is made of a bendable material so that the head portion 13 may be bent laterally relative to the broad faces 13c and 13d using a bending tool as illustrated in FIG. 4.

The angulation head 10 is adapted for use in combination with the submerged functional implant 15 shown in FIG. 3. The implant 15 is of a sharpened blade type having apertures 16, 17 and 18 therein to permit bone growth to penetrate after the implant is inserted in the jaw of the patient, thus permanently securing the insert in the jaw. The lower edge 19 of the blade is sharpened to facilitate entry into the jaw, though such sharpening is not essential. The implant 15 is provided with a relatively short neck portion 20 which together with the blade is adapted to be completely enclosed within a recess, groove or opening formed in the jaw. The neck 20 is hollow and is internally threaded at 21 in order to receive the threaded stem of a temporary cap or permanent head as described in my patent application Ser. No. 819,119, referred to above.

The cap portion 11 of the angulation head 10 is of substantially the same diameter as the outside diameter of the neck portion 20 of the implant 15 and the exteriorly threaded stem 12 is of a size to threadedly engage the threaded bore 21 of the implant. The flat underside 11a of the cap portion 11 is adapted to seat against the flat top 22 of the neck 20 of the implant 15, when the stem 12 is screwed into the hollow neck.

If, after the angulation head 10 is installed on top of the neck 20 of the implant 15, it is determined that the bendable head portion 13 should be bent laterally relative to one of its faces 13c or 13d, the angulation head 10 is removed from the implant 15 and the bending tool 30 shown in FIG. 4 is used to bend the head portion 13.

The bending tool 30 includes an elongated cylindrical threaded holder 31 and an elongated cylindrical bending shaft 32. The threaded holder 31 has an interiorly threaded axial bore 31' which extends inwardly from one end 31" and engages the threaded stem 12 of the angulation head 10 therein with the cap portion 11 seated on the flat end face 31". The bending shaft 32 has an axially extending slot 32' at one end which is of a size and shape to receive the head portion 13 of the angulation head therein. With the angulation head 10 engaged by the threaded holder 31 and the bending shaft as shown in FIG. 4, the head portion 13 may be bent laterally relative to the cap portion 11 by grasping the threaded holder with one hand and the bending shaft with the other hand and applying a bending force.

In FIG. 5, a modified angulation head 40 is shown which has an inverted frusto conical cap 41, a stem 42 depending from the cap 41 and a cylindrical bendable head portion 43. The stem 42 includes an exteriorly threaded tip portion 42a and an unthreaded upper portion 42b intermediate the cap 41 and the tip portion 42a, while the bendable head portion 43 has a hexagonal socket 44 in its free end. The cylindrical stem 43 is adapted to be bent laterally at any angle within a full circle.

The angulation head 40 is adapted to use with an implant 45 (See FIG. 6) which has a short cylindrical neck 46. The neck 46 is hollow and is provided with an interiorly threaded bore 47 at its inner end for threadedly engaging the interiorly threaded tip portion 42a of the angulation head 40, an unthreaded cylindrical counter bore 48 adapted to receive the unthreaded portion 42b and a frusto conical counter-bore 49 adapted to seat the inverted frusto conical cap 41.

For use in bending the modified angulation head 40 as well as for bending the angulation head 10, a modified hand bending tool 50 is shown in FIG. 7. The tool 50 comprises an elongated holder 51 and an elongated bending shaft 52. The holder 51 comprises a linear handle portion 51a having a beveled tip 51b at one end. The tip 51b has a flat end 51c and an axial socket 53 extending inwardly from the flat end 51c. The socket 53 is internally threaded at its inner end to thready engage the threaded stem of either the angulation head 10 or the angulation head 40. An unthreaded counter bore 54 is provided adjacent the flat end 51c to receive the unthreaded stem portion 42b of the angulation head 40. The diameter of the counter bore 54 is slightly greater than the diameter of the unthreaded stem portion 42b of the angulation head 40 so as to provide an annular space 54' between the stem portion 42b and the wall of the counter bore 54 (see FIG. 8).

The bending shaft 52 is a solid elongated cylindrical shaft having an axial cylindrical bore 55 at one end for receiving the cylindrical head portion 43 of the angulation head 40, and a narrow, rectangular axial slot 56 intersecting the cylindrical bore 55 for receiving the head portion 13 of the angulation head 10. The sizes of the bore 55 and of the slot 56 are such as to snugly receive the head portions 43 and 13 of the angulation heads 40 and 10 respectively therein. Thus it will be understood that the bending tool 50 can be selectively used for bending the angulation heads 10 and 40. The thickness of the slot 56, that is, the narrow dimension, is less than the diameter of the cylindrical bore 55.

While in the foregoing there has been described and shown a preferred embodiment of the invention, various modifications and equivalents may be resorted to within the spirit and scope of the invention as claimed.

What is claimed is:

1. The combination comprising an angulation head for removable attachment to a dental implant which has a hollow neck with internal threads in at least a portion of the hollow neck, said angulation head having an intermediate circular flange, a cylindrical stem depending axially from said circular flange, exterior threads on at least a portion of said stem for engagement with the internal threads in said hollow neck, and a bendable elongated head portion extending axially from said flange opposite said stem, and a bending hand tool for bending said bendable head portion of said angulation head, said bending hand tool comprising an elongated holder having a handle portion with a planar end and a socket extending axially inwardly from said flat planar end for holding the stem of said angulation head with said flange abutting said planar end, said socket having an internally threaded portion for threadedly engaging the threaded stem portion of said angulation head, and a hand manipulatable elongated bending shaft having a pair of opposite ends, one end of said bending shaft having an elongated socket extending axially inwardly therefrom which is of a size and shape for snugly receiving the bendable head portion of said angulation head.

2. The combination of claim 1 wherein said elongated socket of said bending shaft includes a central cylindrical socket portion and a thin rectangular slot crossing said cylindrical socket portion, the thickness of said slot being less than the diameter of said cylindrical socket portion.

3. The combination of claim 2 wherein said bendable head portion of said angulation head is cylindrical and is of a diameter slightly less than the diameter of said cylindrical socket portion of said bending shaft so that said bendable head portion fits snugly in said cylindrical socket portion of said bending shaft.

4. The combination of claim 2 wherein said bendable head portion of said angulation head is of thin rectangular cross section having a pair of broad opposite sides and a pair of narrow opposite sides, said rectangular cross-sectioned head portion fitting in the thin rectangular slot of said bending tool.

5. The combination of claim 2 wherein said socket of said elongated holder includes an unthreaded counterbore outwardly of said threaded portion, said unthreaded counterbore being of a diameter greater than the diameter of the stem of said angulation head and providing an annular space between said stem and the wall of said counterbore when said stem is held by said elongated holder.

6. A hand bending tool for bending the bending head portion of a selected one of at least two different angulation heads for dental implants, each of said angulation heads having an intermediate circular flange, a cylindrical stem depending axially from said circular flange, exterior threads on at least a tip end portion of said stem and a bendable elongated head portion extending axially from said flange opposite said stem, the head portion of one of said angulation heads being cylindrical and the head portion of another of said angulation heads being thin and of rectangular cross section, said bending tool comprising an elongated holder having a handle portion with a planar end and a socket extending axially inwardly from said flat planar end for holding the stem of said angulation head with said flange abutting said planar end, said socket having an internally threaded portion for threadedly engaging the threaded stem portion of said angulation head, and a hand manipulatable elongated bending shaft having a pair of opposite ends, one end of said bending shaft having an elongated socket extending axially inwardly therefrom, said elongated socket of said bending shaft including a central cylindrical socket portion of a size for snugly receiving the cylindrical head portion of one of said angulation heads, and a thin rectangular slot crossing said cylindrical socket portion for alternatively receiving the thin rectangular cross-sectioned head portion of another of said angulation heads.

7. The hand bending tool of claim 6 wherein said socket of said elongated holder includes an unthreaded counterbore outwardly of said threaded portion, said unthreaded counterbore being of a diameter greater than the diameter of the stem of said angulation head and providing an annular space between said stem and the wall of said counterbore when said stem is held by said elongated holder.

* * * * *